United States Patent
Shetty et al.

(10) Patent No.: US 9,549,812 B2
(45) Date of Patent: Jan. 24, 2017

(54) BREAST PROSTHESES, METHODS OF MANUFACTURING BREAST PROSTHESES, AND METHODS OF TREATMENT USING BREAST PROSTHESES

(71) Applicant: LIFECELL CORPORATION, Branchburg, NJ (US)

(72) Inventors: Dhanuraj Shetty, Jersey City, NJ (US); Aaron Barere, Hoboken, NJ (US); Evan Friedman, Montvale, NJ (US); Melissa Richter Bowley, Newport, RI (US); Timothy Roock, Bordentown, NJ (US)

(73) Assignee: LifeCell Corporation, Branchburg, NJ (US)

( * ) Notice: Subject to any disclaimer, the term of this patent is extended or adjusted under 35 U.S.C. 154(b) by 0 days.

(21) Appl. No.: 14/371,291

(22) PCT Filed: Jan. 10, 2013

(86) PCT No.: PCT/US2013/021012
§ 371 (c)(1),
(2) Date: Jul. 9, 2014

(87) PCT Pub. No.: WO2013/106556
PCT Pub. Date: Jul. 18, 2013

(65) Prior Publication Data
US 2015/0012089 A1 Jan. 8, 2015

Related U.S. Application Data

(60) Provisional application No. 61/586,391, filed on Jan. 13, 2012.

(51) Int. Cl.
*A61F 2/12* (2006.01)
*A61F 2/00* (2006.01)
(Continued)

(52) U.S. Cl.
CPC ............... *A61F 2/12* (2013.01); *A61F 2/0059* (2013.01); *B29C 65/48* (2013.01);
(Continued)

(58) Field of Classification Search
CPC ............................... A61F 2/12; A61L 27/3604
(Continued)

(56) References Cited

U.S. PATENT DOCUMENTS

| 3,683,424 A | 8/1972 | Pangman |
| 4,298,998 A | 11/1981 | Naficy |

(Continued)

FOREIGN PATENT DOCUMENTS

| DE | 102006029605 A1 | 12/2007 |
| EP | 0338701 A2 | 10/1989 |

(Continued)

OTHER PUBLICATIONS

Baxter; "Intracapsular Allogenic Dermal Grafts for Breast Implant-related Problems": Plast. Reconstr. Surg.; 112(6):1692-1696 (2003).
(Continued)

*Primary Examiner* — Suzette J Gherbi
(74) *Attorney, Agent, or Firm* — McCarter & English, LLP; Matthew R. Van Eman; George Blazeski

(57) ABSTRACT

Improved breast prostheses, methods of making breast prostheses, and methods of treatment using such breast prostheses are described.

19 Claims, 14 Drawing Sheets

(51) Int. Cl.
  *B29C 65/48* (2006.01)
  *B29L 9/00* (2006.01)
  *B29L 31/00* (2006.01)

(52) U.S. Cl.
  CPC . *A61F 2210/0076* (2013.01); *A61F 2220/005* (2013.01); *A61F 2220/0016* (2013.01); *A61F 2220/0033* (2013.01); *A61F 2240/001* (2013.01); *A61F 2250/0031* (2013.01); *B29L 2009/00* (2013.01); *B29L 2031/7532* (2013.01)

(58) Field of Classification Search
  USPC .......................................... 623/7–8
  See application file for complete search history.

(56) References Cited

U.S. PATENT DOCUMENTS

| | | | |
|---|---|---|---|
| 4,840,629 A | 6/1989 | Bustos | |
| 4,936,858 A | 6/1990 | O'Keeffe | |
| 5,066,303 A * | 11/1991 | Bark | A61F 2/12 623/8 |
| 5,352,307 A * | 10/1994 | Wild | B29C 43/18 156/232 |
| 5,356,429 A | 10/1994 | Seare | |
| 5,447,535 A * | 9/1995 | Muller | A61F 2/12 623/8 |
| 5,584,884 A | 12/1996 | Pignataro | |
| 5,658,328 A | 8/1997 | Johnson et al. | |
| 5,658,330 A | 8/1997 | Carlisle et al. | |
| 5,676,161 A | 10/1997 | Breiner | |
| 5,713,959 A | 2/1998 | Bartlett et al. | |
| 5,733,337 A | 3/1998 | Carr, Jr. et al. | |
| 5,755,791 A | 5/1998 | Whitson et al. | |
| 5,954,767 A | 9/1999 | Pajotin et al. | |
| 5,968,096 A | 10/1999 | Whitson et al. | |
| 5,997,575 A | 12/1999 | Whitson et al. | |
| 6,099,566 A | 8/2000 | Vonderharr et al. | |
| 6,203,570 B1 | 3/2001 | Baeke | |
| 6,210,439 B1 | 4/2001 | Firmin et al. | |
| 6,368,541 B1 | 4/2002 | Pajotin et al. | |
| 6,638,308 B2 | 10/2003 | Corbitt, Jr. et al. | |
| 6,666,892 B2 | 12/2003 | Hiles et al. | |
| 6,723,133 B1 | 4/2004 | Pajotin | |
| 6,736,823 B2 | 5/2004 | Darois et al. | |
| 6,736,854 B2 | 5/2004 | Vadurro et al. | |
| 6,740,122 B1 | 5/2004 | Pajotin | |
| 6,802,861 B1 | 10/2004 | Hamas | |
| 7,011,688 B2 | 3/2006 | Gryska et al. | |
| 7,081,135 B2 | 7/2006 | Smith et al. | |
| 7,476,249 B2 | 1/2009 | Frank | |
| 7,658,727 B1 * | 2/2010 | Fernandes | A61F 2/2403 604/265 |
| 7,699,895 B2 | 4/2010 | Hiles et al. | |
| 7,875,074 B2 | 1/2011 | Chen et al. | |
| 8,007,531 B2 | 8/2011 | Frank | |
| 8,128,708 B2 | 3/2012 | Hiles et al. | |
| 8,313,527 B2 * | 11/2012 | Powell | A61F 2/12 623/23.74 |
| 8,487,012 B2 * | 7/2013 | Goraltchouk | A61L 27/18 264/102 |
| 8,685,296 B2 * | 4/2014 | Liu | A61L 27/16 264/344 |
| 8,858,647 B2 | 10/2014 | Markman | |
| 8,876,899 B2 | 11/2014 | Maxwell | |
| 2001/0041936 A1 | 11/2001 | Corbitt et al. | |
| 2002/0103542 A1 | 8/2002 | Bilbo | |
| 2003/0130747 A1 | 7/2003 | Abraham et al. | |
| 2003/0212461 A1 | 11/2003 | Vadurro et al. | |
| 2003/0212462 A1 | 11/2003 | Gryska et al. | |
| 2004/0049269 A1 | 3/2004 | Corbitt et al. | |
| 2004/0260315 A1 | 12/2004 | Dell et al. | |
| 2005/0021141 A1 | 1/2005 | Bleyer et al. | |
| 2005/0165425 A1 | 7/2005 | Croce et al. | |
| 2005/0187624 A1 | 8/2005 | Corbitt | |
| 2005/0250977 A1 | 11/2005 | Montpetit et al. | |
| 2005/0260176 A1 | 11/2005 | Ayares et al. | |
| 2006/0030939 A1 | 2/2006 | Frank | |
| 2006/0167338 A1 | 7/2006 | Shfaram | |
| 2007/0088299 A1 | 4/2007 | Ayre | |
| 2007/0088434 A1 | 4/2007 | Frank | |
| 2007/0116678 A1 | 5/2007 | Sung et al. | |
| 2007/0250177 A1 | 10/2007 | Bilbo | |
| 2008/0027273 A1 | 1/2008 | Gutterman | |
| 2008/0082113 A1 | 4/2008 | Bishop et al. | |
| 2008/0097601 A1 | 4/2008 | Codori-Hurff et al. | |
| 2008/0108134 A1 | 5/2008 | Murphy et al. | |
| 2008/0167729 A1 | 7/2008 | Nelson et al. | |
| 2008/0260853 A1 | 10/2008 | Firestone | |
| 2008/0281418 A1 | 11/2008 | Firestone | |
| 2008/0281419 A1 | 11/2008 | Matheny et al. | |
| 2009/0024227 A1 | 1/2009 | Lesh | |
| 2009/0024228 A1 | 1/2009 | Lesh | |
| 2009/0082864 A1 | 3/2009 | Chen et al. | |
| 2009/0125107 A1 * | 5/2009 | Maxwell | A61F 2/12 623/8 |
| 2009/0198332 A1 | 8/2009 | Becker | |
| 2009/0216338 A1 | 8/2009 | Gingras et al. | |
| 2009/0240342 A1 | 9/2009 | Lindh, Sr. et al. | |
| 2010/0010627 A1 | 1/2010 | Matheny | |
| 2010/0023029 A1 | 1/2010 | Young | |
| 2010/0028396 A1 | 2/2010 | Ward et al. | |
| 2010/0191330 A1 | 7/2010 | Lauryssen et al. | |
| 2010/0217388 A1 | 8/2010 | Cohen et al. | |
| 2010/0226960 A1 * | 9/2010 | Chudzik | A61K 9/0024 424/426 |
| 2011/0022171 A1 | 1/2011 | Richter et al. | |
| 2011/0035004 A1 | 2/2011 | Maxwell | |
| 2011/0177150 A1 * | 7/2011 | Pathak | A61K 35/12 424/422 |
| 2012/0052040 A1 * | 3/2012 | Hunter | A61K 45/06 424/78.3 |
| 2012/0158134 A1 | 6/2012 | Codori-Hurff et al. | |
| 2013/0053956 A1 * | 2/2013 | Powell | A61F 2/12 623/8 |
| 2014/0039617 A1 * | 2/2014 | Maxwell | A61F 2/12 623/8 |
| 2015/0150674 A1 * | 6/2015 | Ansorge | A61F 2/12 623/8 |
| 2015/0223928 A1 * | 8/2015 | Limem | A61F 2/12 623/8 |
| 2015/0359622 A1 * | 12/2015 | Matheny | A61K 35/12 623/23.72 |
| 2015/0359933 A1 * | 12/2015 | Matheny | A61K 35/12 604/93.01 |

FOREIGN PATENT DOCUMENTS

| | | |
|---|---|---|
| JP | 10-158906 | 6/1998 |
| WO | WO-03/084410 A1 | 10/2003 |
| WO | WO-2004/096098 A1 | 11/2004 |
| WO | WO-2006/115892 A2 | 11/2006 |
| WO | WO-2006/135998 A2 | 12/2006 |
| WO | WO-2007/004214 A2 | 1/2007 |
| WO | WO-2008/121816 A2 | 10/2008 |
| WO | WO-2009/114052 A2 | 9/2009 |

OTHER PUBLICATIONS

Bindingnavele et al.; "Use of acellular cadaveric dermis and tissue expansion in postmastectomy breast reconstruction;" Journal of Plastic, Reconstructive & Aesthetic Surgery; 60:1214-1218 (2007).

Breuing et al.; "Immediate Bilateral Breast Reconstruction With Implants and Inferolateral AlloDerm Slings"; Annals of Plastic Surgery; 55(3):232-239 (2005).

Breuing et al.; "Inferolateral AlloDerm Hammock for Implant Coverage in Breast Reconstruction"; Annals of Plastic Surgery; 59(3):250-255 (2007).

Colwell et al.; "Improving Shape and Symmetry in Mastopexy With Autologous or Cadaveric Dermal Slings"; Annals of Plastic Surgery; 61(2):138-142 (2008).

(56) References Cited

OTHER PUBLICATIONS

Darcy; "A Technique for Preparing Meshed Skin Grafts With Planned Expansion Ratios"; British Journal of Plastic Surgery; 56(1):77-79 (2003).
Duncan; "Correction of Implant Rippling Using Allograft Dermis"; Aesthetic Surgery Journal; 21(1):81-84 (2001).
Gamboa-Bobadilla; "Implant Breast Reconstruction Using Acellular Dermal Matrix"; Annals of Plastic Surgery; 56(1):22-25 (2006).
Goes et al.; "The Application of Mesh Support in Periareolar Breast Surgery: Clinical and Mammographic Evaluation;" Aesth. Plast. Surg.; 28:268-274 (2004).
Goes; "Periareolar Mammaplasty with Mixed Mesh Support: The Double Skin Technique;" Operative Techniques in Plastic and Reconstructive Surgery; 3(3):199-206 (Aug. 1996).
Goes; "Periareolar Mammaplasty: Double Skin Technique with Application of Polyglactine or Mixed Mesh"; Plastic and Reconstructive Surgery; 97(5):959-968 (Apr. 1996).
Goes; "Periareolar Mammaplasty: Double Skin Technique with Appliction of Polygractine 910 Mesh"; Rev. Soc. Bras. Cir. Plast. Estet. Reconstr.; 7(1,2,3); pp. 1-6 (1992).
Goes; "Periareolar Mastopexy and Reduction with Mesh Support, Double Skin Technique"; Surgery of the Breast: Principles and Art; Chapter 51; pp. 697-708 (1998).
Goes; "Periareolar Mastopexy: Double Skin Techique with Mess Support"; Aesthetic Surgery Journal; 23:129-135 (Mar./Apr. 2003).
Pope; "Mesh Skin Grafting;" Veterinary Clinics of North America: Small Animal Practice, 20(1):177-187 (Jan. 1990).
Salzberg; "Nonexpansive Immediate Breast Reconstruction Using Human Acellular Tissue Matrix Graft (AlloDerm)"; Annals of Plastic Surgery; 57(1):1-5 (2006).
Topol et al.; "Immediate Single-Stage Breast Reconstruction Using Implants and Human Acellular Dermal Tissue Matrix With Adjustment of the Lower Pole of the Breast to Reduce Unwanted Lift"; Annals of Plastic Surgery; 61(5):494-499 (2008).
Zienowicz et al.; "Implant-based Breast Reconstruction With Allograft"; Plast. Reconstr. Surg.; 120(2):373-381 (2007).

* cited by examiner

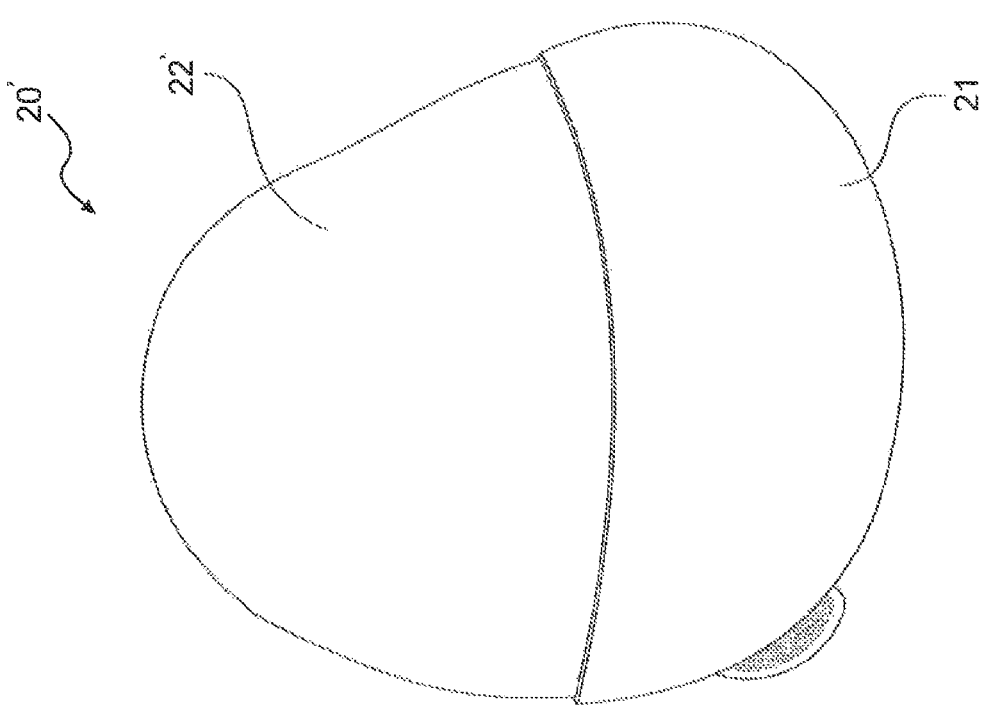

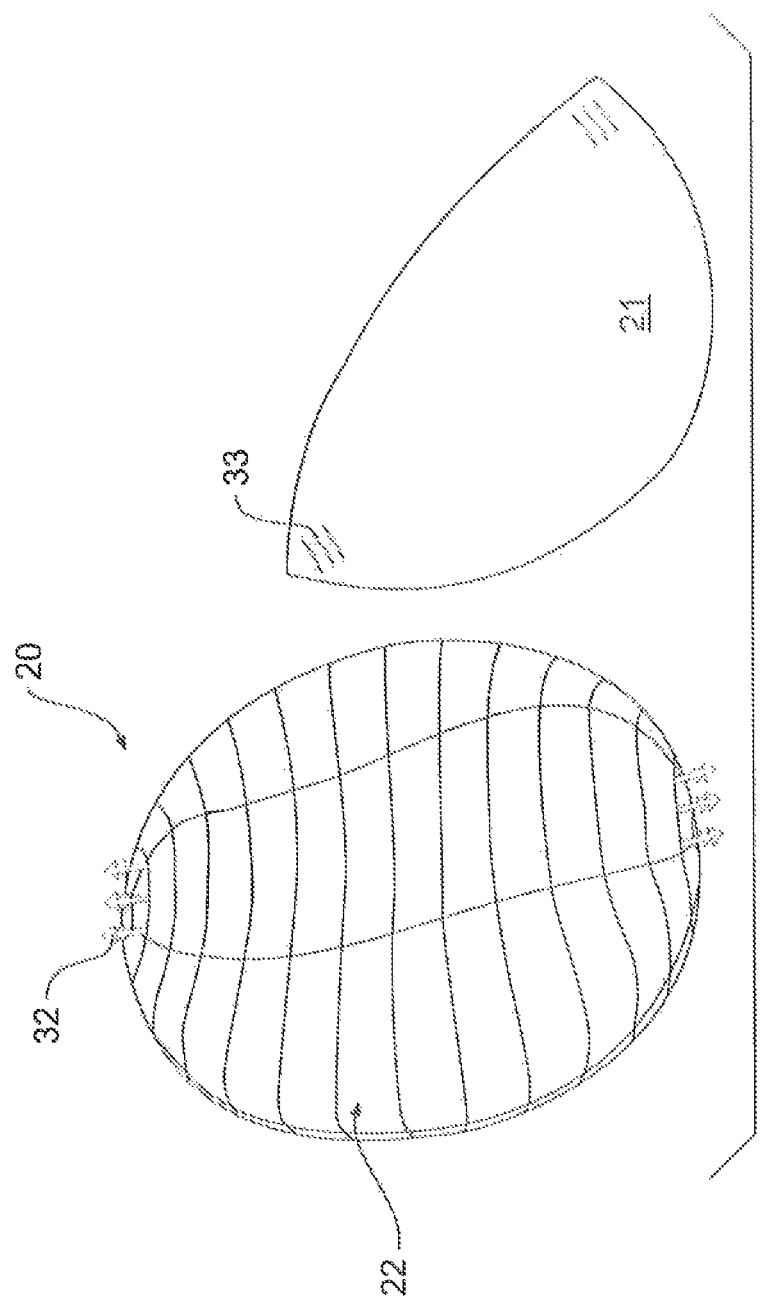

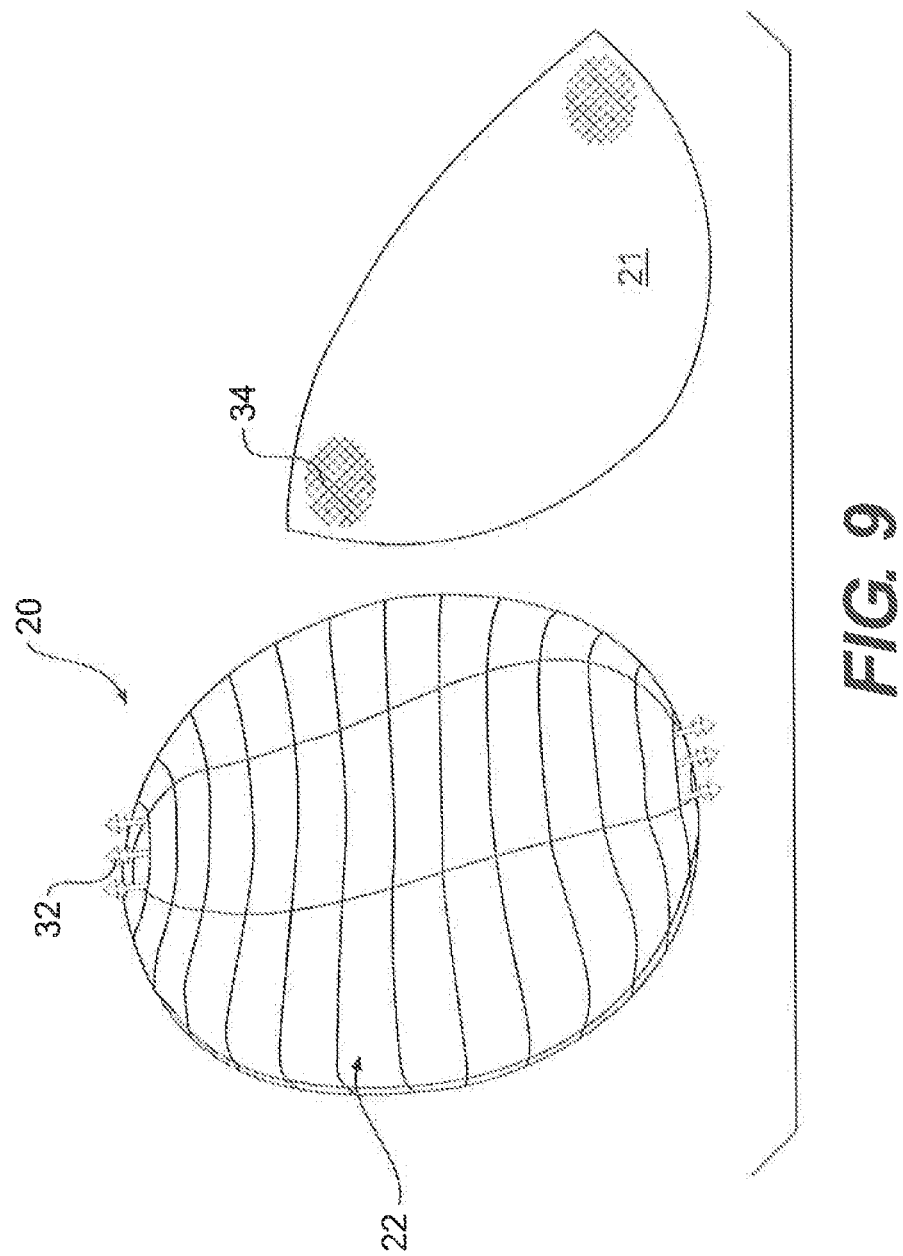

BREAST PROSTHESES, METHODS OF MANUFACTURING BREAST PROSTHESES, AND METHODS OF TREATMENT USING BREAST PROSTHESES

This application is a 35 U.S.C. §371 national stage filing of International Application Number PCT/US2013/021012, which was filed on Jan. 10, 2013 and claims priority under 35 U.S.C. §119 to U.S. Provisional Application No. 61/586,391, which was filed on Jan. 13, 2012. The entire contents of the foregoing applications are incorporated herein by reference in their entirety.

Implantable breast prostheses, such as breast implants and tissue expanders, are used in a wide range of breast surgical procedures. The prostheses can be used for breast augmentation, reconstruction, and/or revision. However, even though the implants and tissue expanders used in breast surgical procedures are biocompatible and non-reactive, post-surgical complications can result from their use. Complications, including capsular contracture, scar formation, implant displacement, rippling, and palpability of implants result in pain and dissatisfaction with breast appearance. Research and studies have been conducted to identify surgical techniques and modified implant characteristics that result in reduced incidence of complications.

One approach that surgeons use to improve aesthetic outcomes, reduce the risk of complications, and or provide improved revisions is to use graft materials, such as acellular dermal tissue matrices such as ALLODERM® or STRATTICE™ (LIFECELL CORPORATION, Branchburg, N.J.), along with the implants or tissue expanders. These tissue matrices can be used to support the breast and to act as a tissue extension or tissue replacement. In addition, by promoting the organization of the healing process, the tissue matrices promote regenerative repair rather than scar formation.

The current standard of care during surgical breast procedures involves separately attaching the graft material to the patient and then placing the prosthesis in the patient. For example, in one procedure the surgeon first separately attaches the graft material to the infra mammary fold (IMF) and the pectoralis major muscle in order to create a submuscular pocket or flap. Next, the surgeon places the breast implant or tissue expander inside the pocket. The entire process of attaching the graft material to the native tissue takes a lot of time and involves the use of many sutures or other devices to anchor the graft material to the native tissue. The current process can also lead to inconsistent results, as inexperienced surgeons may not use graft materials of optimal shape, or may incorrectly position the implant or tissue expander relative to the graft material.

Accordingly, there is a need for an improved breast prostheses, methods of making breast prostheses, and methods of treatment using such breast prostheses.

In accordance with the invention, breast prostheses, methods of making breast prostheses, and methods of treatment using such breast prostheses are provided.

According to certain embodiments, a prosthesis is disclosed that comprises a tissue expander and one or more samples of graft material sized and shaped to conform to a portion of a surface of the tissue expander, wherein the one or more samples of graft material is attached to the tissue expander by an adhesive that degrades over time.

According to certain embodiments, a method of making a prosthesis is disclosed. The method comprises providing a tissue expander and one or more samples of graft material sized and shaped to conform to a portion of a surface of the breast implant or tissue expander, and attaching the one or more samples of graft material to the tissue expander by an adhesive that degrades over time.

According to certain embodiments, a prosthesis is provided. The prosthesis comprises a tissue expander and one or more samples of graft material sized and shaped to conform to a portion of a surface of the tissue expander, wherein the tissue expander comprises resorbable tabs or resorbable barbs, and wherein the one or more samples of graft material are attached to the breast implant or tissue expander by the resorbable tabs or resorbable barbs on the breast implant or tissue expander.

According to certain embodiments, a method of making a prosthesis is provided. The method comprises providing a tissue expander and one or more samples of graft material sized and shaped to conform to a portion of a surface of the tissue expander, wherein the tissue expander comprises resorbable tabs or resorbable barbs, and attaching the one or more samples of graft material to the tissue expander by the resorbable tabs or resorbable barbs on the tissue expander.

According to certain embodiments, methods of making a device suitable for use in breast surgical procedures are provided. The methods comprise providing one or more samples of graft material and forming a pocket from the graft material that is sized and shaped to hold a tissue expander.

According to certain embodiments, methods of making a prosthesis are provided. The methods comprise providing a tissue expander and one or more samples of graft material, forming a pocket from the graft material that is sized and shaped to hold the breast implant or tissue expander, and inserting the implant into the pocket.

According to certain embodiments, methods of making a prosthesis are provided. The method comprise preparing a shell of a tissue expander, providing one or more samples of graft material sized and shaped to conform to a portion of a surface of the tissue expander, attaching the graft material to the outer shell of the tissue expander prior to curing the she of the tissue expander, and curing the combined shell of the tissue expander and graft material. In certain embodiments, the method further comprises the step of removing the graft material from the shell.

Furthermore, methods of treatment using the disclosed prostheses are provided.

BRIEF DESCRIPTION OF THE DRAWINGS

FIG. 1C is a side view of a tissue expander according to certain embodiments.

FIG. 8 is a perspective view of the components of a prosthesis, according to certain embodiments.

FIG. 9 is a perspective view of a prosthesis, according to certain exemplary embodiments.

DESCRIPTION OF CERTAIN EXEMPLARY EMBODIMENTS

Figure 1A:
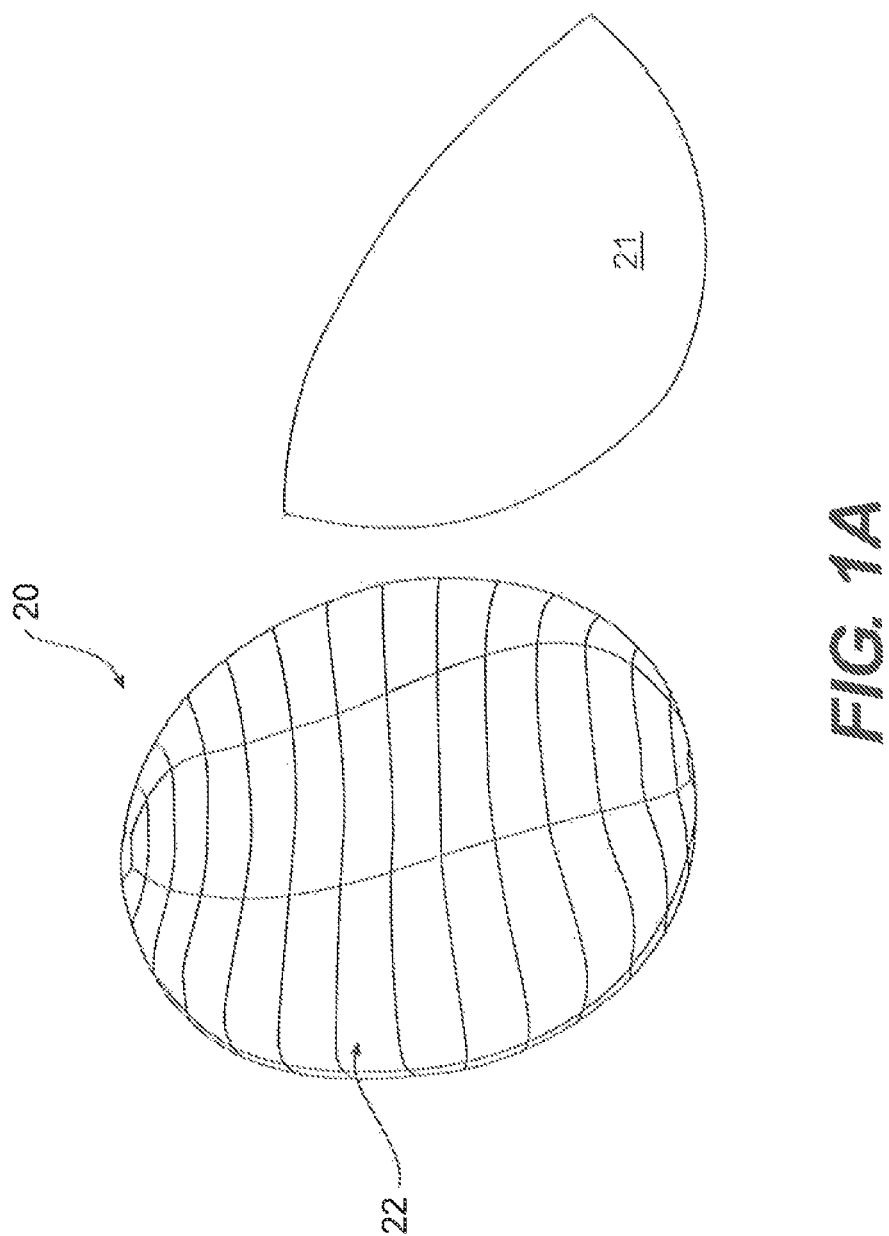
FIG. 1A is a perspective view of the components of a prosthesis according to certain exemplary embodiments.

Reference will now be made in detail to certain exemplary embodiments of the invention, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Any range described herein will be understood to include the endpoints and all values between the endpoints. Also, terms such as "element" or "component" encompass both elements and components comprising one unit and elements and components that comprise more than one subunit, unless specifically stated otherwise. Also, the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "graft material," as used herein, generally refers to a biocompatible material such as, for example, tissue, processed tissue, or synthetics that can be attached to or inserted into a bodily part.

The terms "breast implant" and "implant," as used herein, generally refer to medical devices that are implanted either under or within breast tissue or under the chest muscle for breast augmentation or reconstruction. Such implants can include saline filled or silicone gel implants, or other implants that provide volume for breast augmentation. The terms "breast tissue expander" or "tissue expander," as used herein, generally refer to devices that are implanted under or within breast tissue or chest muscle, and which are expanded over time to stretch breast tissue and skin. Unless otherwise indicated, implants and tissue expanders can be used interchangeably with the graft materials, methods or device of attaching graft materials to implants or expanders, methods of forming implants or graft materials, and methods of treatment or use of the devices described herein. Furthermore, the term "prosthesis" will be understood to include any implantable device disclosed herein, which comprise an implant and/or tissue expander component.

The present disclosure relates to prostheses, methods of making prostheses, and methods of treatment using the prostheses. The prostheses can be used for breast augmentation, reconstruction, or revision. As such, the implantable prostheses and methods discussed herein may be suitable for a wide range of surgical applications. In various embodiments, the prostheses and methods discussed herein may be suitable for various types of surgical breast procedures, such as, for example, aesthetic surgery associated with mastectomy or lumpectomy, breast reconstruction, breast augmentation, breast enhancement, mastopexy, and revisionary breast surgeries.

According to certain embodiments, a prosthesis is disclosed that comprises a breast implant or a tissue expander and one or more samples of graft material, wherein the implant or tissue expander is attached to the one or more samples of graft material in a manner that allows the implant or tissue expander and the one or more samples of graft material to be implanted in a patient as one unitary prosthesis; and wherein the implant or tissue expander is attached to the one or more samples of graft material in a manner that will allow the implant or tissue expander and the graft material to be easily separated after a period of time in vivo.

In certain embodiments, the prosthesis of the present disclosure comprise tissue expanders. Further, the structure of the tissue expander, along with its attachment to a graft material such as an acellular tissue matrix, can allow the tissue expander to be enlarged and removed after a certain period of time, without removing the graft material. Accordingly, the devices and methods of the present disclosure can be beneficial for reconstruction procedures that require removal of tissue expanders.

By providing the implant or tissue expander and the one or more samples of graft material as one unitary prosthesis, the implantable prostheses of the present disclosure can shorten procedure time, reduce the number of surgical sutures and/or staples or other attachment device needed, and reduce the associated costs of surgery. The implantable prostheses can also improve surgical outcomes and improve consistency of results by leveling the playing field for inexperienced surgeons. The implantable prostheses are believed to reduce the incidence of extrusion and capsular contraction, to block the inflammatory response, and to result in shorter expansion times.

However, while in some embodiments the breast implants and tissue expanders can be implanted as one unitary prosthesis, the implantable prostheses of the present disclosure can be constructed such that the breast implant or tissue expander is easily separated from the graft material after being implanted in vivo. In various embodiments, the graft material can be removed from tissue expanders which are designed to be removed from the patient after a period of time, and also for breast implants, which are sometimes removed from the patient for revision, According to certain embodiments, a prosthesis is disclosed that comprises a breast implant or tissue expander and one or more samples of graft material sized and shaped to conform to a portion of a surface of the breast implant or tissue expander, wherein is the one or more samples of graft material is attached to the breast implant or tissue expander by an adhesive that degrades over time. In some embodiments, the adhesive can be a synthetic adhesive. Examples of synthetic adhesives can include silicone, cyanoacrylates, methyl-ethyl cyanoacrylate, iso(n)butyl-cyanoacrylate (Liquid Bandage Vetbond), octyl-cyanoacrylate (DERMABOND), and Polyethylene glycol (PEG) based associated sealants. In some embodiments, the adhesive can be a biologically derived glue. Examples of biologically derived adhesives include marine adhesives, fibrin glue, fibrin sealants (TISSEAL, EVICEL, MOFIBRIX), protein aldehyde sealants (FLOSEAL), mussel adhesive protein, albumin-glutaraldehyde (BIOGLUE).

According to certain embodiments, a method of making a prosthesis is provided. The method can comprise providing a breast implant or a tissue expander and one or more samples of graft material sized and shaped to conform to a portion of a surface of the breast implant or tissue expander, and attaching the one or more samples of graft material to the breast implant or tissue expander with an adhesive that will degrade over time. In some embodiments, the adhesive can be a synthetic adhesive. Examples of synthetic adhesives include silicone, cyanoacrylates, methyl-ethyl cyanoacrylate, iso(n)butyl-cyanoacrylate (Liquid Bandage Vetbond), octyl-cyanoacrylate (DERMABOND), and Polyethylene glycol (PEG) based associated sealants. In some embodiments, the adhesive can be a biologically derived glue. Examples of biologically derived adhesives include marine adhesives, fibrin glue, fibrin sealants (TISSEAL, EVICEL, PROFIBRIX), protein aldehyde sealants (FLOSEAL), mussel adhesive protein, albumin-glutaraldehyde (BIOGLUE).

Figure 1B:
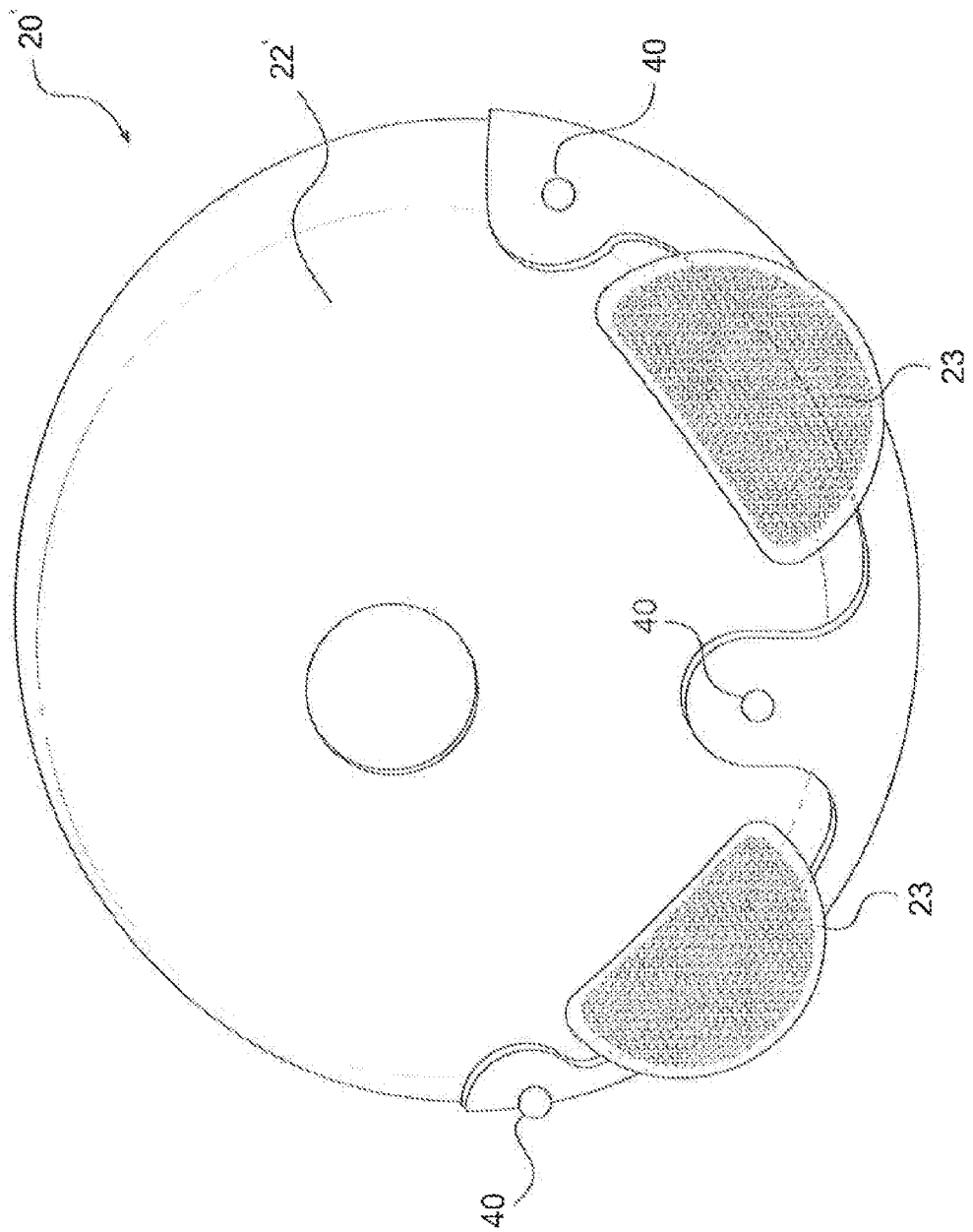
FIG. 1B is a posterior view of a tissue expander according to certain embodiments.
Figure 1D:
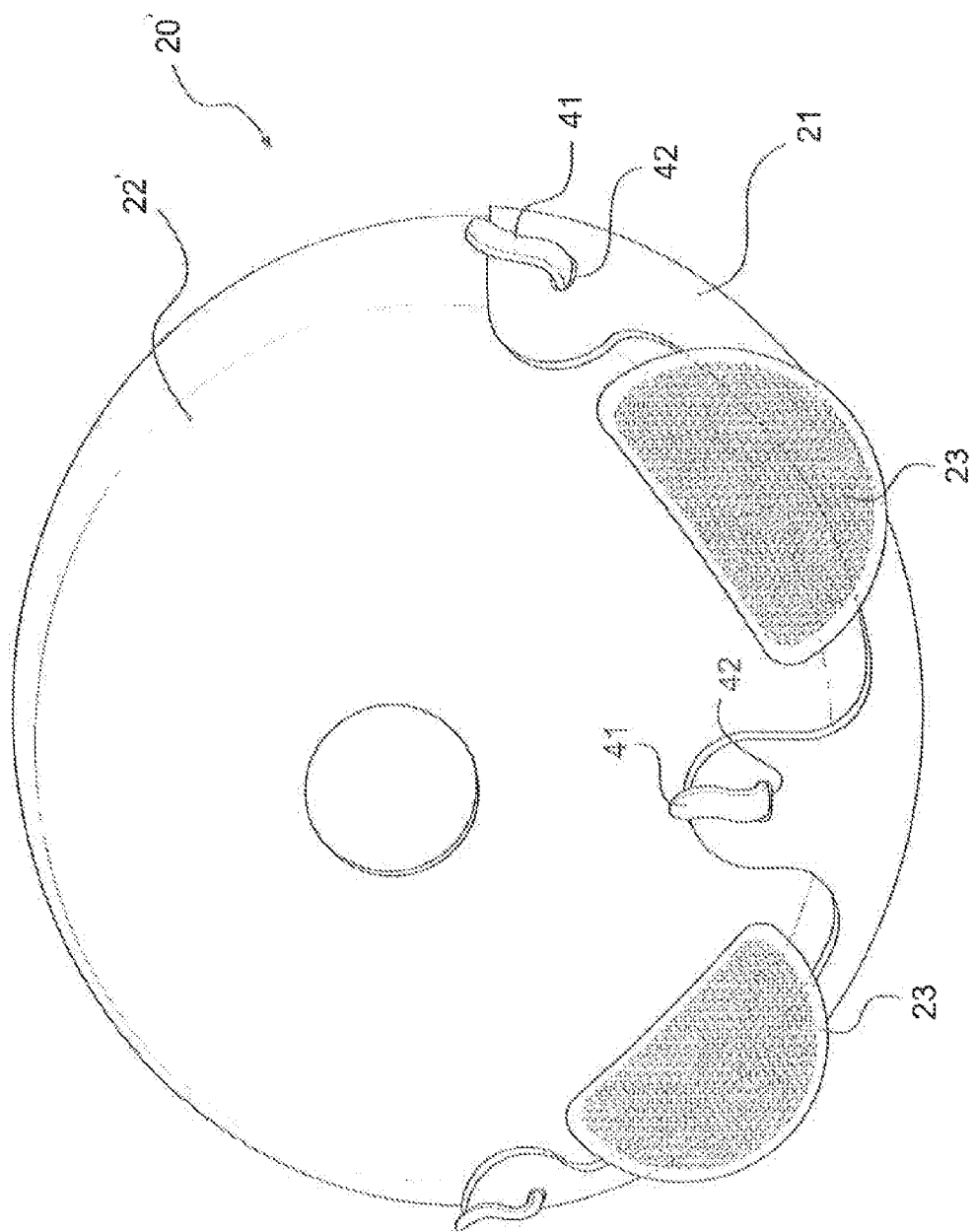
FIG. 1D is a posterior view of a tissue expander according to certain embodiments.

FIG. 1A provides a view of the components of one exemplary embodiment of an implantable prosthesis 20. FIG. 1A shows a modeled Style 410 Anatomical Implant (Allergan, Inc. (Santa Barbara, Calif.)) 22 in a vertical orientation and a sample of graft material 21 having a shape produced by modeling graft material covering 50% of implant 22 such that sample of graft material 21 may be bordered by the inframammary fold, the lateral fold, and the inferior edge of the pectoralis major muscle when implanted in a patient. FIGS. 1A-1C illustrate prostheses 20' comprising tissue expanders 22 with graft materials 21. The tissue expanders 22' can further include suture tabs 23 for attachment of the expander to tissues.

The implants or expanders can be formed from a variety of suitable materials. For example, the shell of an expander may be produced from a material that is designed to prevent tissue ingrowth and adhesion. For example, in some embodiments, the tissue expanders 22' are formed of a smooth shell, such as smooth silicon. Further, the suture tabs 23 can be formed of a textured materials to allow cellular in-growth, or can be formed of a smooth material (e.g., silicone) that prevents adhesion and allows easy removal of the expander later.

In some embodiments the adhesive can be applied directly to the portion of the breast implant 22 or tissue expander 22' that will interface with the graft material 21. In some embodiments the adhesive can be applied directly to the portion of the graft material 21 that will interface with the breast implant 22 or tissue expander 22'. In some embodiments the adhesive can be applied directly to both the portion of the breast implant 22 or tissue expander 22' that will interface with the graft material 21, and to the portion of the graft material 21 that will interface with the breast implant 22 or tissue expander 22'.

In some embodiments, the adhesive can be applied in a spray form over to the portion of the breast implant 22 or tissue expander 22' that will interface with the graft material 21. In some embodiments, the adhesive can be applied in a spray form over the portion of the graft material 21 that will interface with the breast implant 22 or tissue expander 22'.

In some embodiments, the adhesive can be applied in a spray form over both the portion of the breast implant 22 or tissue expander 22' that will interface with the graft material 21, and the portion of the graft material 21 that will interface with the breast implant 22 or tissue expander 22'.

In some embodiments, the breast implant or tissue expander can be attached to the one or more samples of graft material in a surgical setting or the operating room just prior to the prosthesis being implanted in the patient. In some embodiments, the breast implant or tissue expander can be attached to the one or more samples of graft material prior to the surgery. In some embodiments, the breast implant or tissue expander can be attached to the one or more samples of graft material prior to the surgery, so that the implantable prosthesis can be sold as a ready-to-use, off the shelf prosthesis.

According to certain embodiments, a prosthesis is disclosed that comprises a breast implant or tissue expander and one or more samples of graft material sized and shaped to conform to a portion of a surface of the breast implant or tissue expander, wherein the breast implant or tissue expander comprises resorbable tabs or resorbable barbs, and wherein the one or more samples of graft material are attached to the breast implant or tissue expander by the resorbable tabs or resorbable barbs on the breast implant or tissue expander. In various embodiments, the resorbable polymers can comprise aliphatic polyester polymers, copolymers, blends thereof, polymers of lactide, galactide, or copolymers thereof, polysaccharides such as cellulose, and oxidized polysaccharides, or other absorbable polymers.

Figure 2:
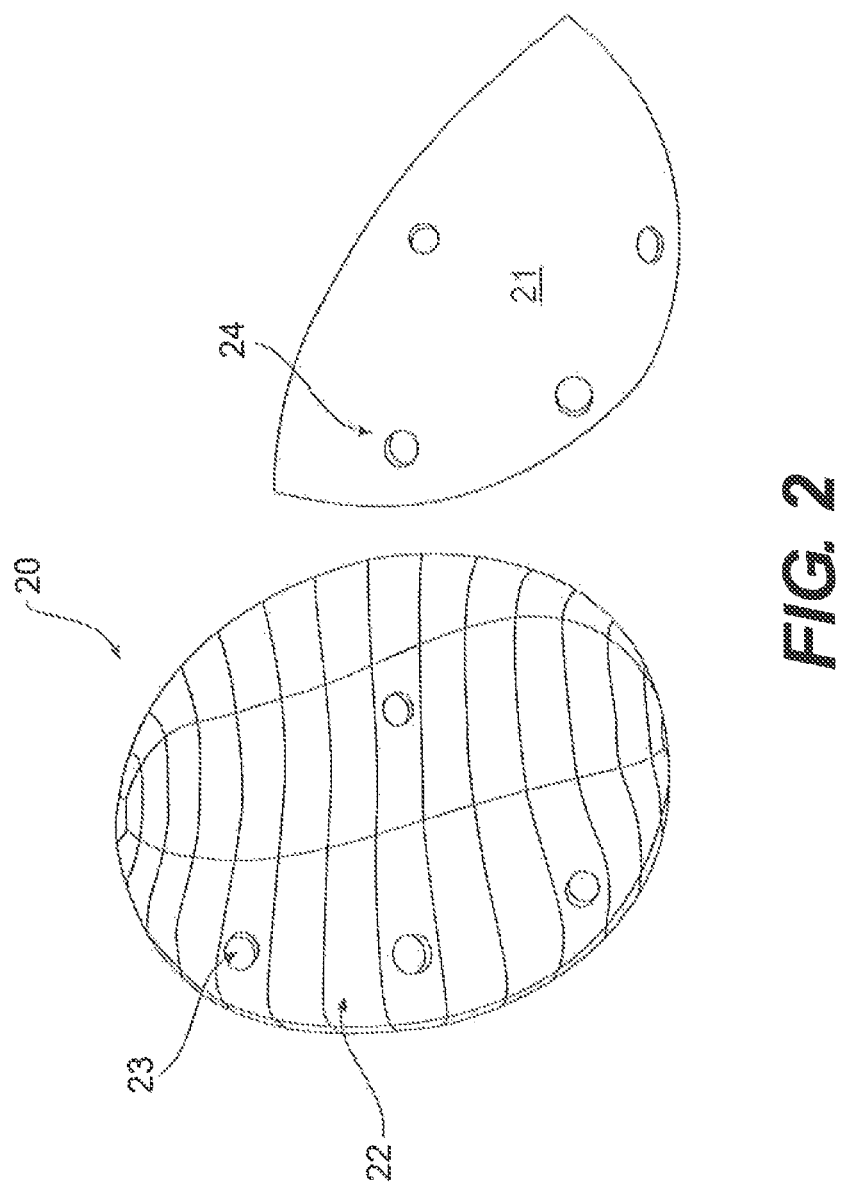
FIG. 2 is a perspective view of the components of a prosthesis according to certain exemplary embodiments.
Figure 3A:
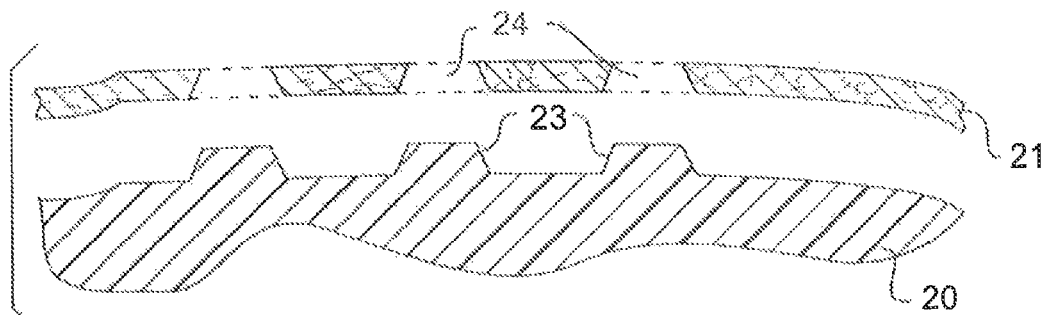
FIGS. 3A and 3B show a schematic view of a portion of graft material and a portion of a breast implant or tissue expander, illustrating how the two components fit together, according to certain embodiments.
Figure 3B:
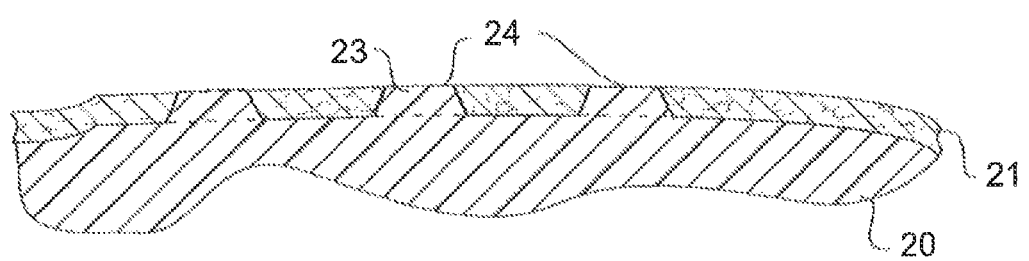
Figure 4A:
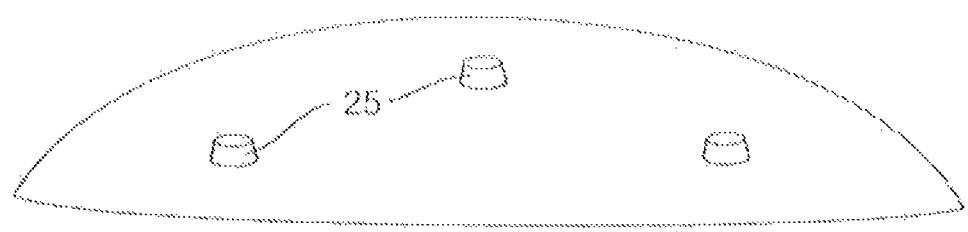
FIGS. 4A, 4B, and 4C show a schematic view a portion of a breast implant or tissue expander, illustrating exemplary shapes of resorbable tabs, according to certain embodiments.
Figure 4B:
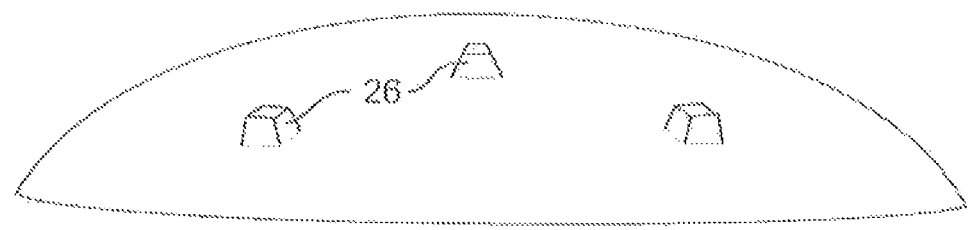
Figure 4C:
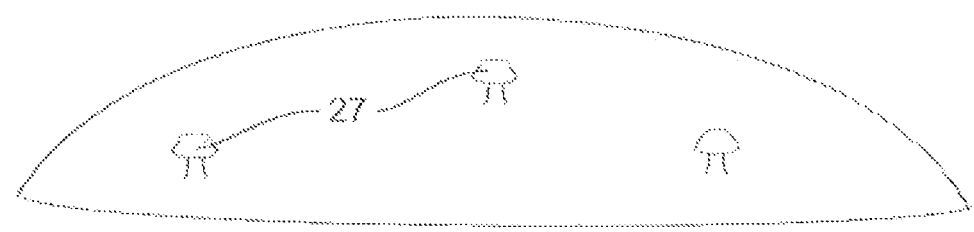

FIG. 2 shows a breast implant 20 in a vertical orientation and a sample of graft material 21. The implant 20 comprises tabs 23. The graft material 21 comprises corresponding apertures 24, so that the graft material can be attached to the implant. FIGS. 3A and 3B depict a schematic view of a portion of the implant 20, resorbable tabs 23, graft material 21, and apertures 24. The tabs can be of any geometrical shape that will engage the graft material. FIGS. 4A, 4B, and 40 show a schematic view a portion of a breast implant, illustrating that the tabs may be circular 25, squared 26, or in the shape of a button 27. In some embodiments, the tabs are placed in a straight line. In some embodiments, the tabs are placed in a non-linear pattern. Furthermore, FIGS. 1A-1C illustrates tissue expanders 21' tabs 40, 41 and openings 42 having configurations that may be used with any of the implants or tissue expanders provided herein.

Figure 5:
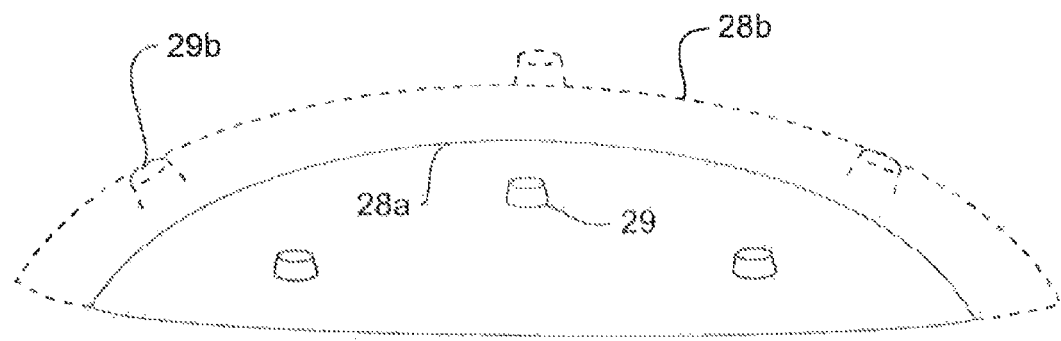
FIG. 5 is a schematic view of a tissue expander, as it expands over time, according to certain embodiments.
Figure 6:
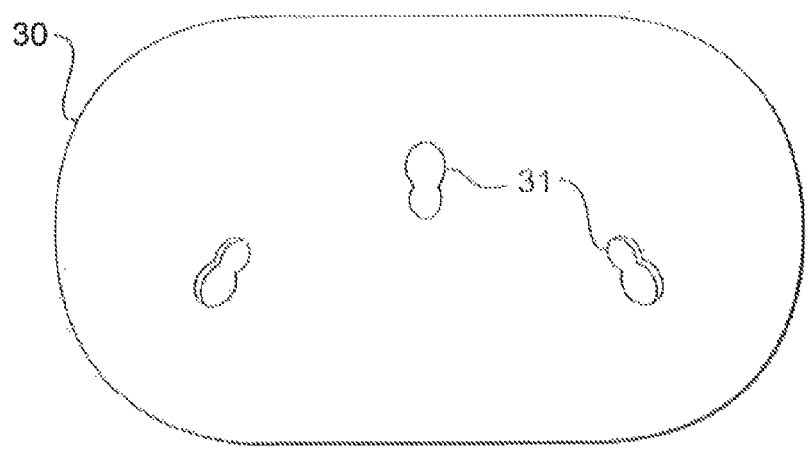
FIG. 6 is a view of a sample of graft material with apertures cut in the graft material that correspond to the tabs on the tissue expander of FIG. 5, according to certain embodiments.

FIG. 5 depicts an exemplary embodiment of a tissue expander 28a that comprises tabs 29a. Over time the tissue expander expands 28b, and the tabs, being located on the surface of the tissue expander, also move to a positio 29b. FIG. 6 depicts a top view of a sample of graft material 30 with apertures 31 cut to leave room for the tissue expander tabs to pop out of the smaller holes and to engage in the larger holes as the tissue expander and tabs expand, as described, for example, with reference to FIG. 5.

Figure 7A:
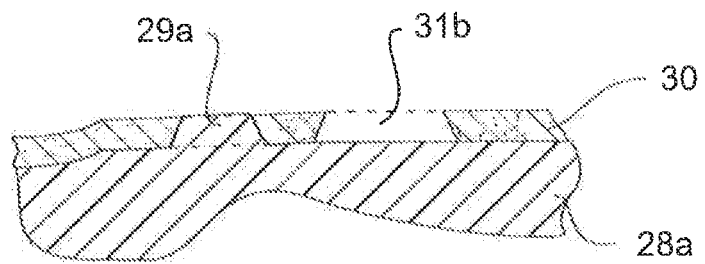
FIGS. 7A, 7B, 7C, 7D, 7E, and 7F show a schematic view of a portion of graft material and a portion of a tissue expander, illustrating how the tabs on the tissue expander pop out of a smaller hole in the graft material, and fit into the larger hole on the graft material, as the tissue expander expands, according to certain embodiments.
Figure 7B:
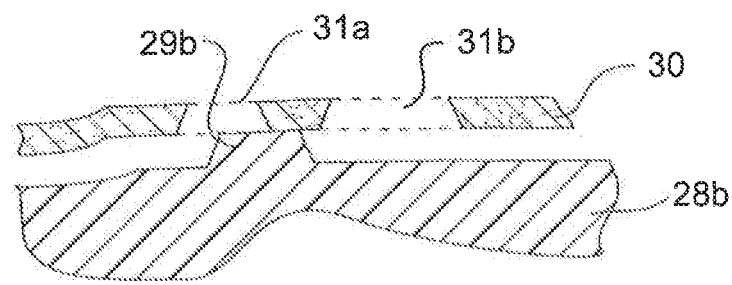
Figure 7C:
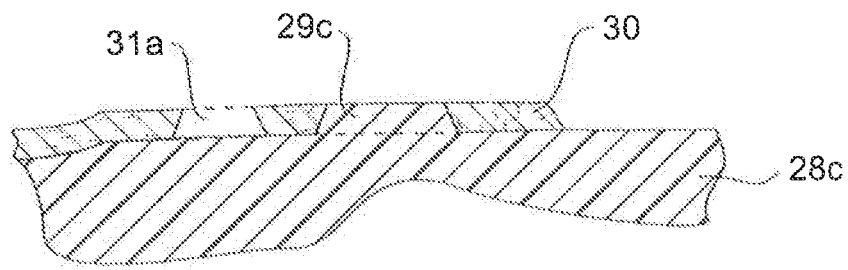
Figure 7D:
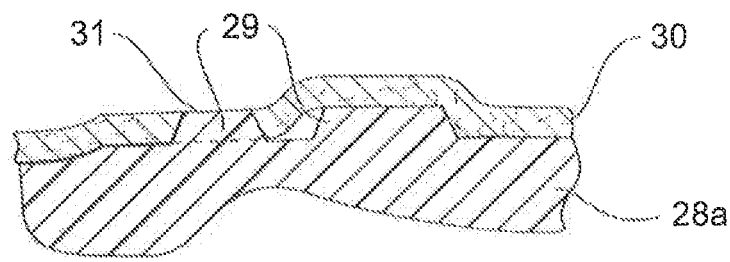
Figure 7E:
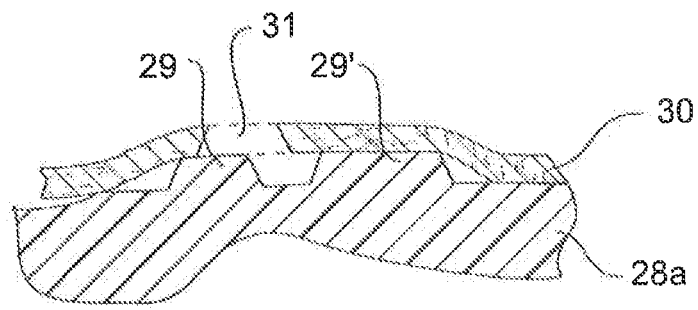
Figure 7F:
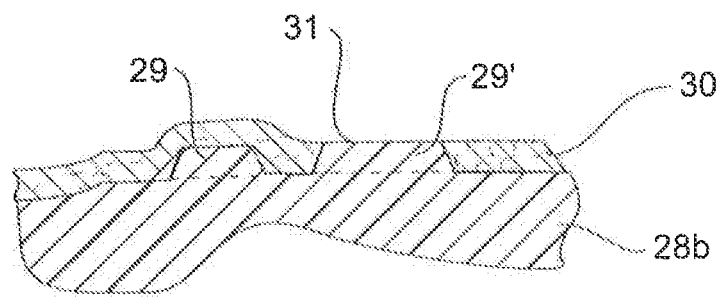

FIGS. 7A-7C depict a schematic side view of a portion of a tissue expander 28a and graft material 30. Over time, as the tissue expander volume increases 28b (FIG. 7B) and 28c (FIG. 7C), the location of the tabs increases 29b and 29c, and the tissue expander tab 29a pops out of the smaller hole 31a, and attaches firmly to the larger hole 31b. Further, in certain embodiments, as shown in FIGS. 7D-7F, the expander 28 can have tabs 29, 29' of differing sizes, which can accommodate differing sizes of aperatures 31, which may stretch or enlarge as the tissue expanding enlarges.

In some exemplary embodiments, the graft material does not comprise apertures, and the graft material is attached to the resorbable tabs by biodegradable sutures, adhesives that degrade over time, or any means of attachment known by one of skill in the art.

In some embodiments, the implant or tissue expander comprises resorbable barbs. FIGS. 8 and 9 depict exemplary embodiments, wherein the implant 20 or tissue expander comprises resorbable barbs 32, which attach to slits 33 (FIG. 8) or mesh 34 (FIG. 9) on the graft material.

According to certain embodiments, a method of making an implantable prosthesis is disclosed. The method can comprise providing a breast implant or tissue expander and one or more samples of graft material sized and shaped to conform to a portion of a surface of the breast implant or tissue expander, wherein the breast implant or tissue expander comprises resorbable tabs or resorbable barbs, and attaching the one or more samples of graft material to the breast implant or tissue expander by the resorbable tabs or resorbable barbs on the breast implant or tissue expander.

In some embodiments, the breast implant or tissue expander can be attached to the one or more samples of graft material in a surgical setting or the operation room just prior to insertion. In some embodiments the breast implant or tissue expander can be attached to the one or more samples of graft material prior to the surgery. In some embodiments the breast implant or tissue expander can be attached to the one or more samples of graft material prior to the surgery, so that the implantable prosthesis can be sold as a ready-to-use, off the shelf prosthesis.

According to certain embodiments, methods of making a device suitable for use in breast surgical procedures are disclosed comprising providing one or more samples of graft material and forming a pocket from the graft material that is sized and shaped to hold a breast implant or tissue expander.

Figure 10B:
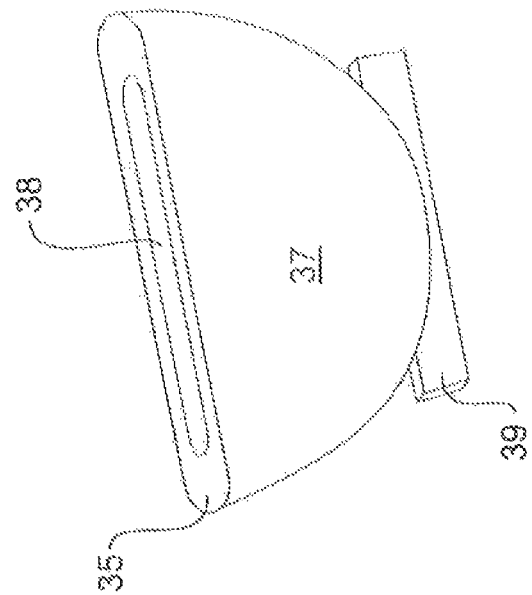
FIGS. 10A and 10B are perspective views of graft material according to certain exemplary embodiments.
Figure 10A:
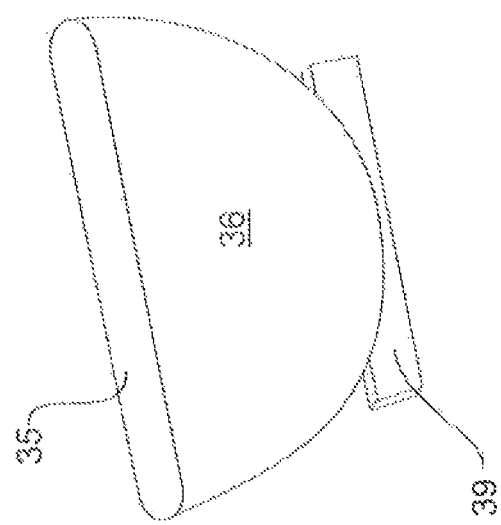
Figure 11A:
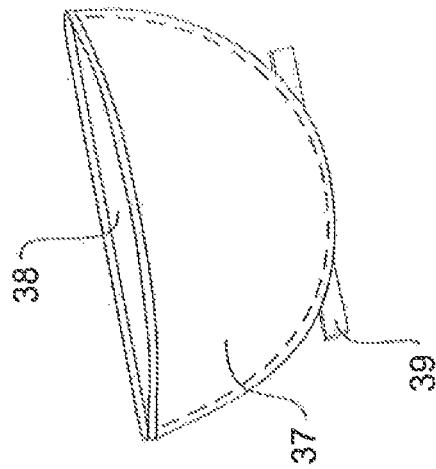
FIGS. 11A and 11B are perspective views of graft materials according to certain exemplary embodiments.
Figure 11B:
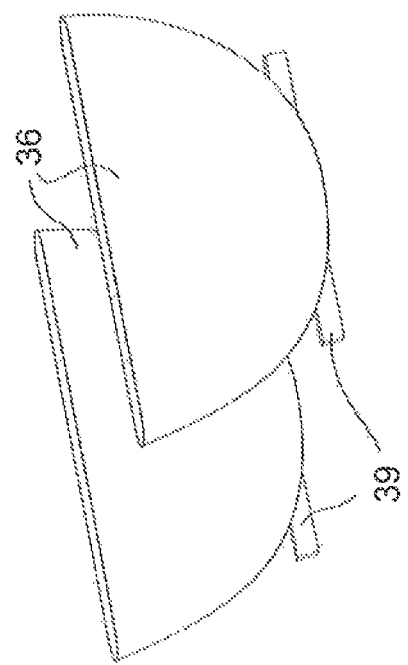

FIGS. 10A and 10B illustrate the components of one exemplary embodiment. According to certain embodiments, the pocket may be formed by cutting a slit through the thickness 35 of the graft material 36, forming a pocket 37 with an open end 38. FIGS. 11A and 11B illustrate the components of another exemplary embodiment. According to certain embodiments, the pocket may be formed by cutting two portions of graft material 36 and attaching the portion with an adhesive, sutures, or any other means known to one of skill in the art to form a pocket 37 with an open end 38.

In some embodiments, the pocket further comprises suture tabs 39, for attachment of the pocket to the chest wall.

According to certain embodiments, methods of making a prosthesis are disclosed comprising providing a breast implant or tissue expander and one or more samples of graft material, forming a pocket from the graft material that is sized and shaped to hold the breast implant or tissue expander, and inserting the implant into the pocket.

According to certain embodiments, methods of making a prosthesis are disclosed comprising preparing the shell of a silicone breast implant or silicone tissue expander, providing one or more samples of graft material sized and shaped to conform to a portion of a surface of a breast implant or tissue expander, attaching the graft material to the shell of the breast implant prior to curing the shell of the silicone breast implant or silicone tissue expander, and curing the shell of the breast implant or tissue expander and the graft material.

In some embodiments the graft material is an acellular tissue matrix. In some embodiments the shell of the breast implant or tissue expander and the acellular tissue matrix are cured such that the curing temperature does not reach a temperature greater than 30° C. In some embodiments the shell of the breast implant or tissue expander and the acellular tissue matrix are cured such that the curing temperature does not exceed 25° C.

In some embodiments the graft material is an adipose extracellular tissue matrix protein that has been treated to produce a three-dimensional porous, or sponge-like material. In some embodiments the shell of the breast implant or tissue expander and the adipose extracellular tissue matrix are cured such that the curing temperature is between 70° C. to 120° C., or between 80° C. to 110° C., or to about 100° C. In some embodiments lower or higher temperatures could be used as long as melting of the matrix proteins does not occur.

In certain embodiments the method of making a prosthesis further comprises the step of removing the graft material from the shell after the curing step but prior to implanting the prosthesis. This step results in a silicone breast implant or tissue expander with the texture of the graft material impressed on the implant.

The various embodiments of implantable prostheses discussed herein include a sample of graft material. The graft materials discussed herein include a sample of biocompatible material. The samples of biocompatible material can comprise any suitable synthetic or biologic material, such as, for example, medical grade silicon, autologous or cadaveric tissue, and/or biomatrices, such as, for example, an acellular tissue matrix ("ATM"). In some embodiments, the sample of biocompatible material may be a flat sheet or sheet-like in form. A sample of biocompatible material may be a single layer or ay be multi-layered. In some embodiments, a sample of biocompatible material may be a material that facilitates revascularization and cell repopulation. For example, certain embodiments can include an acellular tissue matrix ("ATM").

As used herein, ATM refers to a tissue-derived biomatrix structure that can be made from any of a wide range of collagen-containing tissues by removing all, or substantially all, viable cells and all detectable subcellular components and/or debris generated by killing cells. As used herein, an ATM lacking "substantially all viable cells" is an ATM in which the concentration of viable cells is less than 1% (e.g., less than: 0.1%; 0.01%; 0.001%; 0.0001%; 0.00001%; or 0.000001%) of that in the tissue or organ from which the ATM was made.

In some embodiments the ATM is treated to produce a three-dimensional porous, or sponge-like material.

For a description of ATMs that are suitable for use in the present disclosure, as well as methods of making ATMs, see copending U.S. application Ser. No. 12/506,839 (published as US 2011/0022171) at paragraphs 41-73 and U.S. Provisional Application No. 61/491,787 at paragraphs 23-38 and 42-56. The disclosure of both applications is incorporated herein by reference in their entirety. Additionally, as non-limiting examples of methods of producing ATMs, mention is made of the methods described in U.S. Pat. Nos. 4,865,871; 5,366,616; and 6,933,326, and U.S. Patent Application Publication Nos. US2003/0035843 A1, and US 2005/0028228 A1, all of which are incorporated herein by reference in their entirety.

In some embodiments, the graft material comprises STRATTICE™, a porcine dermal tissue produced by Lifecell Corporation (Branchburg, N.J.). In some embodiments, the graft material comprises ALLODERM®, an ATM produced from human dermis by the LifeCell Corporation (Branchburg, N.J.).

In some embodiments, the graft material comprises an adipose tissue matrix. In some embodiments the graft material is an adipose extracellular tissue matrix protein that has been treated to produce a three-dimensional porous, or sponge-like material. For a description of adipose tissue matrices that are suitable for use in the present disclosure, as well as methods of making adipose tissue matrices, see copending U.S. Provisional Application No. 61/491,787 at paragraphs 23-38 and 42-56. Briefly, the process generally includes obtaining adipose tissue, mechanically processing the adipose tissue to produce small pieces, further processing the tissue to remove substantially all cellular material and/or lipids from the tissue, resuspending the tissue in a solution to form a porous matrix or sponge, and cross-linking the tissue to produce a stable three-dimensional structure.

In certain embodiments, ready-to-use, off-the-shelf graft materials that are designed to conform to breast implants of various specifications can be used. For a description of methods of making graft materials that are sized and shaped to conform to a portion of a surface of the breast implant and are suitable for use in the present disclosure, see copending U.S. application Ser. No. 12/506,839 (published as US 2011/0022171). The disclosure of U.S. application Ser. No. 12/506,839 is incorporated herein by reference in its entirety.

In certain embodiments, methods of treatment are provided comprising providing any one of the breast prostheses described above; and implanting the breast prosthesis into a site on a patient where a breast prosthesis is required.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A prosthesis comprising a tissue expander and one or more samples of graft material, wherein the tissue expander comprises resorbable tabs and the one or more samples of graft material comprise apertures, and wherein the one or more samples of graft material are attached to the tissue expander by engaging the resorbable tabs on the tissue expander to the apertures on the one or more samples of graft material.

2. A method of making an implantable prosthesis comprising providing a tissue expander and one or more samples of graft material, wherein the tissue expander comprises resorbable tabs and the one or more samples of graft material comprise apertures; and
    attaching the one or more samples of graft material to the tissue expander by causing the resorbable tabs on the tissue expander to engage the apertures on the one or more samples of graft material.

3. A method of making an implantable prosthesis comprising preparing a shell of a silicone breast implant or tissue expander;
    providing one or more samples of graft material sized and shaped to conform to a portion of a surface of the breast implant or tissue expander, wherein the graft material is an adipose extracellular tissue matrix that has been treated to produce a three-dimensional porous, or sponge-like material;
    attaching the graft material to the shell of the breast implant or tissue expander prior to curing the shell of the silicone breast implant or tissue expander; and
    curing the shell of the breast implant or tissue expander and the graft material.

4. The method of claim 3, wherein the graft material is an acellular tissue matrix.

5. The method of claim 4, wherein the shell of the breast implant or tissue expander and the adipose acellular tissue matrix are cured such that the curing temperature does not reach a temperature greater than 30° C.

6. The method of claim 4, wherein the shell of the breast implant or tissue expander and the adipose acellular tissue matrix are cured such that the curing temperature does not exceed 25° C.

7. The method of claim 3, wherein the shell of the breast implant or tissue expander and the adipose extracellular tissue matrix are cured at a temperature between 80° C. to 110° C.

8. The method of claim 3, wherein the graft material is removed from the breast implant or the tissue expander after the curing step.

9. A prosthesis comprising a tissue expander and one or more samples of graft material, wherein the tissue expander comprises resorbable barbs and the one or more samples of graft material comprise slits, and wherein the one or more samples of graft material are attached to the tissue expander by engaging the resorbable barbs on the tissue expander to the slits on the one or more samples of graft material.

10. A prosthesis comprising a tissue expander and one or more samples of graft material, wherein the tissue expander comprises resorbable barbs and the one or more samples of graft material comprise mesh, and wherein the one or more samples of graft material are attached to the tissue expander by engaging the resorbable barbs on the tissue expander to the mesh on the one or more samples of graft material.

11. A method of making an implantable prosthesis comprising providing a tissue expander and one or more samples of graft material, wherein the tissue expander comprises resorbable barbs and the one or more samples of graft material comprise slits; and
    attaching the one or more samples of graft material to the tissue expander by engaging the resorbable barbs on the tissue expander to the slits on the one or more samples of graft material.

12. A method of making an implantable prosthesis comprising providing a tissue expander and one or more samples of graft material, wherein the tissue expander comprises resorbable barbs and the one or more samples of graft material comprise mesh; and
    attaching the one or more samples of graft material to the tissue expander by engaging the resorbable barbs on the tissue expander to the mesh on the one or more samples of graft material.

13. A method of making an implantable prosthesis comprising preparing a shell of a silicone breast implant or tissue expander;
    providing one or more samples of graft material sized and shaped to conform to a portion of a surface of the breast implant or tissue expander;
    attaching the graft material to the shell of the breast implant or tissue expander prior to curing the shell of the silicone breast implant or tissue expander;
    curing the shell of the breast implant or tissue expander and the graft material; and
    removing the graft material from the breast implant or tissue expander after the curing step.

14. The method of claim 13, wherein the graft material is an acellular tissue matrix.

15. The method of claim 14, wherein the shell of the breast implant or tissue expander and the acellular tissue matrix are cured such that the curing temperature does not reach a temperature greater than 30° C.

16. The method of claim 14, wherein the shell of the breast implant or tissue expander and the acellular tissue matrix are cured such that the curing temperature does not exceed 25° C.

17. The method of claim 13, wherein the graft material is an adipose extracellular tissue matrix that has been treated to produce a three-dimensional porous, or sponge-like material.

18. The method of claim 17, wherein the shell of the breast material or tissue expander and the adipose extracellular tissue matrix are cured at a temperature between 80° C. to 110° C.

19. The method of claim 13, wherein the graft material is removed from the breast implant or tissue expander after the curing step.

* * * * *